United States Patent [19]
Arnett et al.

[11] 4,284,573
[45] Aug. 18, 1981

[54] PREPARATION OF GLYCIDYL ETHERS

[75] Inventors: John F. Arnett, Newton; George A. Doorakian, Bedford, both of Mass.

[73] Assignee: The Dow Chemical Company, Midland, Mich.

[21] Appl. No.: 80,769

[22] Filed: Oct. 1, 1979

[51] Int. Cl.$^3$ .......................................... C07D 301/28
[52] U.S. Cl. .......................... 260/348.15; 260/348.19
[58] Field of Search .................. 260/348.15, 348.18, 260/348.19

[56] References Cited

U.S. PATENT DOCUMENTS

| 3,948,855 | 4/1976 | Perry | 260/47 EP |
| 3,992,432 | 11/1976 | Napier et al. | 260/348.31 |
| 3,996,259 | 12/1976 | Lee et al. | 260/348.18 |

FOREIGN PATENT DOCUMENTS

| 893191 | 7/1970 | Canada | |
| 2335199 | 1/1975 | Fed. Rep. of Germany | 260/348.15 |
| 2533505 | 12/1976 | Fed. Rep. of Germany | 260/348.15 |
| 1019565 | 2/1966 | United Kingdom | 260/348.15 |

OTHER PUBLICATIONS

Chemical Abstracts, vol. 87 (1977) 22359X.

Primary Examiner—Norma S. Milestone
Attorney, Agent, or Firm—Michael L. Glenn

[57] ABSTRACT

A process for producing glycidyl ethers of phenols is described which comprises the steps of:
(1) reacting by contacting, in liquid phase, a phenol with excess epichlorohydrin in the presence of a catalytic amount of tetrahydrocarbyl phosphonium bicarbonate salt, to thereby produce a coupled reaction product comprising the corresponding propylenechlorohydrin ether of said phenol;
(2) devolatilizing said coupled reaction product to remove excess epichlorohydrin and volatile by-products; and
(3) contacting the devolatilized reaction product from Step (2) with aqueous base, thereby converting the propylenechlorohydrin groups of the coupled reaction product to glycidyl ether groups.

This process is particularly useful in preparing low molecular weight liquid epoxy resins by the reaction of epichlorohydrin with bisphenol A.

10 Claims, No Drawings

PREPARATION OF GLYCIDYL ETHERS

BACKGROUND OF THE INVENTION

1. Field of the Invention

This invention pertains to a process of making glycidyl ethers of phenolic compounds by the reaction of epichlorohydrin with the phenols. More particularly, this invention pertains to a process for making low molecular weight liquid epoxy resins from the reaction of epichlorohydrin with polyhydric phenols.

2. Prior Art

The prior art is replete with techniques of preparing glycidyl ethers of phenols and particularly for preparing glycidyl ethers of polyhydric phenols.

The usual preparation of glycidyl ethers of phenols involves the reaction of epichlorohydrin with a phenol in the presence of an alkali metal hydroxide, as represented by the following equation:

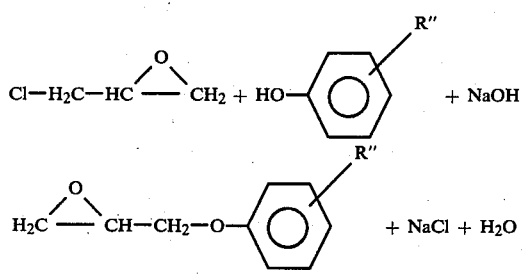

The stoichiometry of the reaction requires one equivalent of epichorohydrin and one equivalent of base per phenolic hydroxyl group. However, excessive amounts of undesirable by-products are produced if one uses a stoichiometric ratio of reactants. To maximize the yield of the glycidyl ether, excess epichlorohydrin and excess base have been used to a substantial advantage. One of the major problems associated with the use of excess epichlorohydrin has been the recovery of unreacted epichlorohydrin from the reaction product.

A typical multistep method for preparing glycidyl ethers of phenols which results in the production of low molecular weight epoxy resins is described in U.S. Pat. No. 2,943,095 (Farnham et al.). Farnham et al. conducted the reaction of epichlorohydrin with a polyhydric phenol in two steps: In the first step, the phenol is reacted with excess epichlorohydrin in the presence of a base (e.g., lithium chloride, lithium acetate and alkali metal hydroxides) to give a product comprising the propylene chlorohydrin of the phenol. This reaction is generally referred to as the coupling reaction. Farnham et al. report that in stage one, the reaction temperature should not exceed 45° C. In step two, the coupled reaction product is dehydrohalogenated with a strong base to form the corresponding glycidyl ether of the phenol. This dehydrohalogenation is normally performed in a mixture of liquids comprising a volatile water-soluble alcohol or ketone and a water-immiscible liquid. Farnham et al. recover excess epichlorohydrin by distillation between steps one and two.

Many other patents have issued which also use a multistep reaction and which teach that various catalysts may be used to promote the coupling reaction.

Reinking et al. (U.S. Pat. No. 2,943,096) indicate that the coupling step is greatly facilitated by conducting the reaction under anhydrous conditions in the presence of a quaternary ammonium salt catalyst. This reference teaches that the coupling reaction should be conducted at temperatures less than 60° C. At temperatures in excess of 60° C., undesirable polymeric compounds are formed.

Others have utilized sulfonium salts (e.g., British Pat. No. 1,019,565), tertiary amines or quaternary ammonium salts as catalysts for the coupling reaction (e.g., British Pat. No. 897,744) and still others have utilized phosphonium salts (German AUS. No. 2,335,199) and/or phosphoranes (e.g., German Offen. No. 2,533,505). The latter two German references are the closest prior art relative to step one in the instant process in that these references do at least use catalysts containing phosphorus.

The dehydrochlorination step has also been the subject of investigation. Smith (U.S. Pat. No. 3,372,442) teaches that the dehydrochlorination is facilitated by using an aqueous sodium hydroxide solution which is substantially saturated with sodium carbonate. Becker (U.S. Pat. No. 3,980,679) teaches that the dehydrochlorination is facilitated by adding solid alkali metal hydroxide incrementally to the reaction mixture.

None of the aforementioned references teach that there is any advantage in conducting the dehydrochlorination step in the presence of a quaternary onium salt nor do they indicate what effect, if any, the residual quaternary onium salts or other catalysts have on the reaction product or on this particular step of the overall reaction. It is known, however, that amines and quaternary ammonium salts are capable of causing degradation of the epoxides. And at least one of the references specifically teaches that the catalyst for the coupled reaction should be removed from the reaction mixture prior to the dehydrochlorination reaction (British Pat. No. 897,744). The other references are not as explicit in their written description but convey the same teaching in that they wash the coupling reaction product with water to remove the catalyst and/or water-soluble by-products, (e.g., sodium chloride and other salts) before the dehydrochlorination step. Still other references handle the problem by passing the glycidyl ether of the phenol through various clays or other materials to absorb the residual catalyst from the reaction product.

The glycidyl ethers of phenols can be prepared according to the above techniques using either batch processes or by continuous processes. This is illustrated by the above references and by German Pat. No. 2,522,745 and German Pat. No. 2,523,696.

SUMMARY OF THE INVENTION

A process for producing glycidyl ethers of phenols has now been discovered which comprises the steps of:

(a) introducing a catalytic amount of a tetrahydrocarbyl phosphonium bicarbonate salt into a liquid phase mixture of a phenol with excess epichlorohydrin to thereby produce at reactive conditions a coupled reaction product comprising the corresponding propylenechlorohydrin ether of said phenol; and (b) contacting the coupled reaction product in a liquid organic solvent with sufficient aqueous base in the presence of a catalytic amount of the tetrahydrocarbyl phosphonium bicarbonate salt or its in situ derivative salts from step (a) to convert the propylenechlorohydrin groups to the corresponding glycidyl ether groups.

The glycidyl ethers prepared in the above-described manner are advantageous because of their excellent color and purity. Epoxy resins produced by this process moveover have the advantage of a low total organic chloride content and a narrow molecular weight distribution that corresponds closely to theory.

DETAILED DESCRIPTION OF THE INVENTION

Phosphonium Bicarbonate Salts

The tetrahydrocarbyl phosphonium bicarbonate salts correspond to the formula I

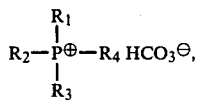

wherein $R_1$, $R_2$, $R_3$ and $R_4$ independently are hydrocarbyl or inertly-substituted hydrocarbyl radicals, having from 1 to about 20 carbon atoms. $R_1$, $R_2$, $R_3$ and $R_4$ are preferably $C_1$ to $C_{12}$ alkyl groups or phenyl and more preferably are $C_1$ to $C_4$ alkyl or phenyl. More preferably $R_1$-$R_3$ are each phenyl groups and $R_4$ is an n-butyl group. Most preferably $R_1$-$R_3$ are each n-butyl groups and $R_4$ is a methyl group.

Compounds of the formula I are conveniently prepared by reacting at room temperature a tetrahydrocarbyl phosphonium halide dissolved in a lower alkanol with an ion-exchange resin (quaternary ammonium hydroxide type), to thereby produce a solution containing the corresponding tetrahydrocarbyl phosphonium hydroxide salt. Carbon dioxide at a positive pressure is then brought into intimate contact with the alkanoic solution of the phosphonium hydroxide salt at room temperature so as to produce the tetrahydrocarbyl phosphonium bicarbonate salt.

Illustrative examples of the instant class of catalysts include those of formula I wherein $R_1$-$R_4$ are each ethyl, n-butyl, hexyl, octyl, phenyl, benzyl, hydroxymethyl, cyanoethyl, and the like. Other illustrative examples include those of formula I in which $R_1$-$R_4$ are different. For example, those in which $R_1$ is n-butyl, $R_2$ is phenyl, $R_3$ is phenyl and $R_4$ is methyl.

PHENOLIC REACTANTS

The phenols, wich are used herein, are a known class of organic compounds having one or more hydroxyl groups attached to an aromatic mono- or polycyclic hydrocarbon nucleus. This class of compounds includes phenol, alpha- and beta-naphthol, o-, m-, or p-chlorophenol, alkylated derivatives of phenol (e.g., o-methyl-, 3,5-dimethyl-, p-t-butyl- and p-nonylphenol) and other monohydric phenols, as well as polyhydric phenols, such as resorcinol, hydroquinone, phloroglucinol, bis(4-hydroxyphenyl)-2'-hydroxyphenyl methane (i.e. tris-phenol),etc. The polyhydric phenols bearing from 2 to 6 hydroxyl groups and having from 6 to about 30 carbon atoms are particularly useful in the reaction with epichlorohydrin to form epoxy resins useful in coatings. Particularly preferred polyhydric phenols are those corresponding to the formula

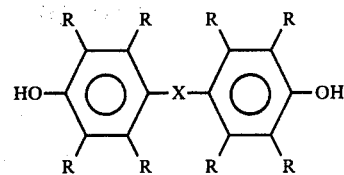

wherein each R independently is hydrogen, halogen (fluoro, chloro or bromo) or a hydrocarbyl radical and X is oxygen, sulfur, —SO—, —$SO_2$—, bivalent hydrocarbon radicals containing up to about 10 carbon atoms, and oxygen-, sulfur- and nitrogen-containing hydrocarbon radicals, such as —OR'O—, —OR'OR'O—, —S—R'—S—, —S—R'—S—R'—S—, —OSiO—, —OSiOSiO—,

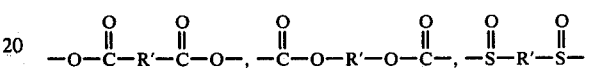

and —$SO_2$—R'—$SO_2$—radicals wherein R' is a bivalent hydrocarbon radical. 4,4'-Isopropylidenediphenol (i.e., bisphenol A) is the most preferred phenol.

COUPLING REACTION: STEP (A)

The process for preparing glycidyl ethers of phenols consists of two distinct reactions—coupling (Step (a)) and dehydrochlorination (Step (b)). These reactions can be carried out in a batch, semi-continuous or continuous process.

The so-called "coupling reaction" is the reaction between a phenol and epichlorohydrin to produce the corresponding propylenechlorohydrin ether of the phenol, as shown by the equation:

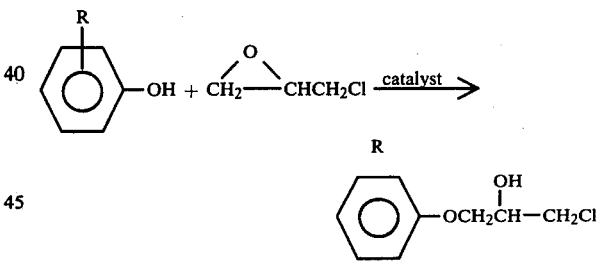

wherein R is a univalent organic radical. Preferably, R is hydrogen, alkyl, aryl, (hydroxyar)alkyl, (hydroxyar)-thiol or bis(hydroxyar)alkyl. This reaction also produces other by-products. The propylenechlorohydrin ether in turn can react with a second equivalent of epichlorohydrin to produce a minor amount of 1,3-dichloropropanol and the glycidyl ether of the phenol.

The coupling reaction is carried out in a liquid phase, normally with mixing. Convenient rates of reaction have been observed at a temperature of from about 40° to about 200° C., preferably from about 75° to about 160° C.

A catalytic amount of the phosphonium bicarbonate salt is introduced into the reaction medium. The term catalytic amount as used in Step (a) refers to an amount of the phosphonium bicarbonate salt introduced which effects an increase in the rate of the coupling reaction. The phosphonium bicarbonate salt desirably effects this rate increase, without producing substantial self-polymerization of the epichlorohydrin. In this utility, the amount of catalyst introduced can be varied over a wide range. Generally, however, it is used in quantities from about 0.001 to about 10 percent by weight, based on the combined weight of reactants. Preferably, the catalyst is included in amounts of from about 0.05 to about 5 percent by weight.

It is believed, but not yet proven, that the bicarbonate counterion of the phosphonium salt exchanges to some extent in situ during the coupling and dehydrochlorination reactions with other proton donating species (HA), such as the phenol reactant or water and alkanol diluents, as shown by the equation:

$$R_1R_2R_3R_4P^{\oplus}HCO_3^{\ominus} + HA \rightleftharpoons R_1R_2R_3R_4P^{\oplus}A^{\ominus} + H_2O + CO_2$$

Therefore, the actual catalyst species may consist of tetrahydrocarbyl phosphonium bicarbonate, hydroxide, alkoxide, phenoxide salts or mixtures thereof. For the sake of brevity, these possible catalyst species are termed tetrahydrocarbyl phosphonium bicarbonate and its in situ derivative salts.

The ratio of the reactants is desirably at least about 1.5, preferably greater than about 2.5, equivalents of epichlorohydrin per phenolic hydroxyl group. To facilitate removal of excess epichlorohydrin (i.e., that epichlorohydrin in excess of a stoichiometric amount) and minimize by-products, the ratio of reactants is desirably less than about 20, preferably less than about 10, equivalents of epichlorohydrin per phenolic hydroxyl group. The manner in which the reactants are brought together is not critical, so long as the aforementioned ratios are effected.

The reactants at operable temperatures and ratios are generally present in the liquid phase, hence no other solvent or dispersive medium is needed. However, solvents inert in the reaction can be employed as desired to improve heat transfer, dispersion of the reactants, to facilitate the introduction of the individual reactants or catalyst into the reaction medium, or to achieve other purposes desired by the skilled artisan. It is preferable, but not essential that an excess of epichlorohydrin be employed as the solvent.

Generally, it is desirable for reasons of economy to convert all or substantially all of the phenol reactant to the corresponding propylenechlorohydrin ether. The reaction time required to attain an equilibrium state in which substantially all (i.e., greater than about 98 mole percent) of the phenol is converted to the coupled reaction product depends upon the reaction temperature, the particular phenol reactant and other factors. Typically, the reaction time to attain the equilibrium state for reaction temperatures from 75° C. to 160° C. is between 0.25 and 6 hours.

At equilibrium, the reaction medium contains in addition to the propylenechlorohydrin ether of the phenol, various phosphonium salts, epichlorohydrin, minor amounts of the glycidyl ether of the phenol, 1,3-dichloropropanol and other by-products. Because hydrolyzable chlorine greater than 400 parts per million by weight or total organic chlorine content greater than about 0.6 weight percent can have a deleterious effect on the properties of an epoxy resin product, it is important that most of the organic chlorine be removed from the glycidyl ether products to be employed as epoxy resins. It is desirable, but not essential to remove the 1,3-dichloropropanol and excess epichlorohydrin by vacuum distillation of the equilibrium mixture resulting from the coupling reaction prior to the dehydrochlorination reaction. Caustic treatment of the 1,3-dichloropropanol maximizes the recovery of epichlorohydrin for recycle. However, it is also operable to distill the product mixture only after the dehydrochlorination reaction.

DEHYDROCHLORINATION REACTION: STEP (B)

The dehydrochlorination reaction or so-called "epoxidation" reaction conducted in the presence of an aqueous base produces a glycidyl ether from the corresponding propylenechlorohydrin ether of the phenol with the concomitant formation of a stoichiometric amount of a salt of the base. This reaction is carried out with mixing in a liquid water-immiscible organic medium at a temperature less than 175° C., preferably from about 25° to about 150° C., with an aqueous base and in the presence of a catalytic amount of the phosphonium bicarbonate salt or its in situ derivative salts from step (a). For reasons of convenience, it is preferred that the in situ derivative salts of the phosphonium bicarbonate from step (a) be employed in step (b). However, it is also operable to add a catalytic amount of a tetrahydrocarbyl phosphonium bicarbonate salt directly to the reactants.

The dehydrochlorination reaction medium includes two phases—a substantially water-immiscible organic phase and an aqueous phase having a basic pH. The organic phase can operably consist essentially of the equilibrium reaction mixture resulting from the coupling reaction. Alternatively, the organic phase can operably be the devolatized coupling reaction mixture. However, preferably the coupled reaction medium is first distilled to remove the more volatile organic chlorine compounds and then a sufficient quantity of an organic hydrocarbon solvent is added to the devolatized or substantially devolatized coupled reaction product to dissolve said product. The organic hydrocarbon solvent should be inert in the dehydrochlorination reaction and should, of course, dissolve the coupled reaction product. Representative compounds which are generally suitable as solvents include lower chlorinated alkanes, such as methylene chloride and the like, and aromatic hydrocarbons, such as toluene, and the like.

The aqueous base acts as an acceptor for the hydrogen chloride produced by the dehydrochlorination reaction. Suitable hydrochloric acid acceptors include both inorganic and organic bases, but the water-soluble inorganic hydroxides are preferred due to cost, ease of handling, their inactivation of the phosphonium salt catalyst after a period of contact, etc. Representative bases include sodium and potassium hydroxides, sodium and potassium carbonates, sodium and potassium phosphates, triethylamine, pyridine, and the like. Sodium hydroxide is the preferred base because of its commercial availability and relative cost.

The term catalytic amount as used in Step (b) refers to an amount of the phosphonium bicarbonate salt or its in situ derivative salts which effects an increase in the rate of dehydrochlorination. The identity of the hydrocarbyl substituents borne by phosphorus in the tetrahydrocarbyl phosphonium bicarbonate or its in situ derivative salts is relevant in determining the catalytic activity of the phosphonium salt in the dehydrochlorination reaction. It has been discovered that $(n-C_4H_9)_3P^{\oplus}CH_3 \ HCO_3^{\ominus}$, $(C_6H_5)_3P^{\oplus}-n-(C_4H_9) HCO_3^{\oplus}$ and to a lesser extent $(C_6H_5)_3P^{\oplus}CH_3 \ HCO_3^{\ominus}$ (wherein $C_6H_5$ is phenyl at each occurrence) and their in situ derivatives from step (a) all act as phase-transfer catalysts which enhance the rate of the dehydrochlorination reaction. The skilled artisan can readily determine as necessary whether other specific tetrahydrocarbyl phosphonium bicarbonate or its in situ derivative salts not explicitly named herein possess the requisite catalytic activity in the disclosed process by preparing epoxy resins as disclosed in the examples. The quantity of catalyst employed in the dehydrochlorination reaction can vary over a wide range. Conveniently, the quantity of catalyst is substantially the same as that employed in the preceding coupling reaction and is simply carried over in the reaction medium employed in this coupling reaction.

The phosphonium salt during contact with the aqueous base in the dehydrochlorination reaction reacts to produce the corresponding phosphine oxide in the following manner:

$$(R)_4P^{\oplus}A^{\ominus} + NaOH \rightarrow (R)_3P=O + NaA + RH$$

The fact that the phosphine oxide is not effective as a catalyst in the dehydrochlorination reaction is both an advantage and disadvantage. Advantageously, because the presence of the deactivated catalyst residue in the glycidyl ether product does not create stability or end-use problems, it is unnecessary to remove the deactivated catalyst from the product. However, the effectiveness of the particular phosphonium salt in catalyzing the biphasic dehydrochlorination will depend upon the relative rates of dehydrochlorination and degradation of the catalyst to the phosphine oxide. Therefore, with some tetrahydrocarbyl phosphonium salt catalyst species which degrade relatively rapidly, such as tri(phenyl)methylphosphonium bicarbonate, it is necessary to utilize a relatively larger initial quantity of the phosphonium bicarbonate or in situ derivative salt catalyst or to introduce catalyst intermittently during the course of the dehydrochlorination reaction to provide a catalytic amount of the salt to substantial completion of the reaction.

The time required to effect substantially complete dehydrochlorination of the propylene chlorohydrin of the phenol depends primarily upon the reaction temperature, the character of the particular chlorohydrin and the identity and quantity of the catalyst present. Typically, the reaction time to effect substantially complete epoxidation for reaction temperatures from 25° C. to 150° C. is between 0.2 and 4 hours, the reaction proceeding more rapidly at relatively higher temperatures. Of course, in those end uses in which it is desirable to first deactivate the catalyst, a longer contact time may be desirable.

After the dehydrochlorination reaction is complete the product is conveniently recovered by first separating the organic layer from the aqueous phase and then washing the organic phase with water until a neutral wash substantially free of ionic chloride is obtained. The washed organic phase is then distilled at reduced pressure to remove solvent and any residual volatile organic chloride compounds from the glycidyl ether of the phenol.

Reaction Products

The glycidyl ether of phenols here produced are generally known compounds in industry. These glycidyl ethers of phenols are generally useful as reactive intermediates in the preparation of coatings, adhesives, reinforced plastics, moldings, etc. In particular, the polyglycidyl ethers of polyhydric phenols, such as the diglycidyl ether of bisphenol A, and the di- or triglycidyl ether of phloroglucinol are useful as epoxy resins. These epoxy resins can be reacted with polyhydric phenols or polycarboxylic acids in the manner described in U.S. Pat. Nos. 3,477,990 and 4,048,141 to prepare a variety of useful compositions.

The following examples further illustrate the invention. All parts and percentages are by weight unless otherwise specified.

EXAMPLE 1

Preparation of (n—$C_4H_9$)$_3$P$^{\oplus}_{CH_3}$ HCO$_3^{\ominus}$

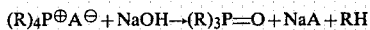

A solution of 100 grams of tri(n-butyl)methyl phosphonium bromide salt in 40 grams of methanol is percolated through a tightly packed column of 509 grams of a quaternary ammonium-type, styrenedivinylbenzene anion exchange resin (sold under the tradename Dowex ® SBR) bearing 3.5 milliequivalents per gram of exchangeable hydroxide groups. The methanol solution is found by conventionl methods of analysis to contain 17 percent of tri(n-butyl)methyl phosphonium hydroxide salt and containing only 0.05 percent bromine.

To the methanol solution of $$(n—C_4H_9)_3P^{\oplus}CH_3OH^{\ominus},$$

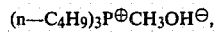

6.07 grams of water is added with stirring at room temperature. Gaseous carbon dioxide is then sparged through the solution until 14.85 grams has been absorbed. After stirring the solution for one hour, the methanol solvent is then distilled under reduced pressure to yield 92.7 grams of a colorless crystalline solid. Conventional methods of analysis (infrared spectroscopy, proton and phosphorus nuclear magnetic resonance spectroscopy) are utilized to identify the product as tri(n-butyl)methyl phosphonium bicarbonate salt. The yield of this product based on the corresponding bromide is 99.0 mole percent.

EXAMPLE 2

Preparation of Epoxy Resins

To a reaction vessel equipped with an internal stirrer and a means for recording temperature is charged 228 grams (1.0 mole) of 4,4'-isopropylidenediphenol (bisphenol A), 1387.5 grams (15.0 moles) of epichlorohydrin and 18.5 grams of a 30 percent solution of tri(n-butyl)methylphosphonium bicarbonate salt (0.02 moles) in an aqueous, methanol medium. The stirred reaction mixture is heated from 20° C. to 150° C. and held at the latter temperature for 1 hour. The unreacted epichlorohydrin and the reaction by-product 1,3-dichloropropanol is then distilled from the reaction mixture at reduced pressure.

The distilled reaction product is dissolved at 20° C. in an equal weight of methylene chloride and combined with 489 grams of an 18 percent solution of aqueous sodium hydroxide. The stirred biphasic mixture is heated to 75° C. and maintained at this temperature for 0.5 hour. The organic and aqueous phases are separated and the organic layer is washed with water until the aqueous wash has a neutral pH. The methylene chloride is then removed by distillation to yield 328.8 grams of an off-white (Gardner 2) viscous liquid. The yield of this product based on the bisphenol A is 96.7 mole percent.

The observed epoxy content of the resin product determined by conventional wet analysis technique is 23.6 percent; almost identical to the theoretical value of 24 percent obtained if all the product is present as the diglycidyl ether of bisphenol A. The epoxy equivalent weight of the product is 182 and the viscosity is 8500 centipoise at 25° C. The resin product contains 0.26 percent total chlorine with less than 37 parts per million (ppm) hydrolyzable chlorine as determined by titration with silver nitrate in the conventional manner. The resin also contains less than 50 ppm phenolic hydroxyl groups. A linear epoxy resin was thus provided having low viscosity, very low color and low residual phenolic-hydroxyl and chloride contents.

EXAMPLE 3

In a manner similar to that described in Example 2 (except for the reaction times and temperatures and the use of an epichlorohydrin solvent in the epoxidation reaction), a stirred mixture of 22.8 grams (0.1 mole) of p,p'-bisphenol A, 74 grams (0.8 mole) of epichlorohydrin and 1.85 grams of an aqueous, methanol solution of 30 percent tri(n-butyl)methylphosphonium bicarbonate salt is heated from 20° C. to 105° C. and maintained at the latter temperature for about 4 hours. At 20° C., 48.8 grams of an 18 percent aqueous solution of sodium hydroxide is added to the reaction mixture and then the stirred mixture is heated to 45° C. for 3 hours. The organic phase of the reaction mixture is separated and washed with water until the aqueous wash has a neutral pH. The excess epichlorohydrin and other volatile components are then distilled from the product to yield 30.01 grams of an off-white (Gardner 2) viscous liquid product. The yield of this product based on the bisphenol A is 88.4 mole percent. The observed epoxy content of the resin product is 21.58 percent.

EXAMPLE 4

In a manner similar to that described in Example 2, a stirred mixture of 22.8 grams (0.1 mole) of industrial-grade bisphenol A (90–98 percent p,p'-bisphenol A and a remaining amount of other isomers), 74 grams (0.8 mole) of epichlorohydrin and 1.85 grams of an aqueous, methanol solution of 30 percent tri(n-butyl)methyl phosphonium bicarbonate salt (0.002 mole) is heated from 20° C. to 105° C. and maintained at the latter temperature for about 4 hours. The reaction by-product 1,3-dichloropropanol and the unreacted epichlorohydrin is then distilled from the reaction mixture at reduced pressure.

The distilled reaction product is dissolved at 20° C. in 80 milliliters of toluene and combined with 100 milliliters of a 12 percent solution of aqueous sodium hydroxide. The stirred biphasic mixture is refluxed for 2.5 hours and then the organic layer is separated and washed with water. Finally, the toluene is removed by distillation to yield a light yellow (Gardner 3) viscous epoxy resin in 95 mole percent yield based on bisphenol A.

The observed epoxy content of the resin product is 22.8 percent and the epoxy equivalent weight is 187. The viscosity of the resin is 11,500 centipoise at 25° C. and resin is determined by conventional methods of analysis to contain a total chlorine content of 0.29 percent and less than 100 ppm of phenolic hydroxyl.

EXAMPLE 5

A precatalyzed epichlorohydrin mixture is prepared by combining 740 grams of epichlorohydrin with 26 grams of a 30 weight percent solution of tri(n-butyl)-methyl phosphonium bicarbonate salt in an aqueous, methanol solvent. In a manner otherwise similar to Example 2, 76.6 grams of the precatalyzed mixture (0.8 mole of epichorlohydrin) is added to 22.8 grams (0.1 mole) of (p,p'bisphenol A) at 20° C. The stirred reaction mixture is heated to 105° C. and held at the latter temperature for 4 hours. The mixture is devolatilized by distillation at reduced pressure and then dissolved in methylene chloride.

The dehydrochlorination reaction and product recovery is performed in the manner described in Example 2 to yield 33.58 grams of almost colorless (Gardner 2) product. The yield of this product based on the bisphenol A is 98.8 mole percent. The observed epoxide content and epoxy equivalent weight are 23.02 percent and 187, respectively. The product contains a total chlorine content of 0.28 percent with 65 ppm hydrolyzable chlorine and 50 ppm phenolic hydroxyl groups. The viscosity of the freshly-prepared resin is 10,500 centipoise at 25° C. and increases to only 10,625 centipoise at 25° C. after storage for 2 weeks at 25° C., which indicates excellent room temperature stability.

In order to demonstrate the high temperature stability of the instant resin product, 5.29 grams of epoxy resin grade bisphenol A (97 percent of p,p'-bisphenol A and 3 percent o,p'-bisphenol A) is added to 10 grams of liquid resin to produce a mixture having an observed epoxy content of 14.92 percent. After heating the mixture to 160° C. for 3 hours, the epoxy content of the mixture is determined to be 12.06 percent.

COMPARATIVE EXPERIMENT

In a manner otherwise identical to Example 4, 0.002 mole of a prior art coupling catalyst, benzyltrimethylammonium chloride (BTMAC), is utilized instead of the tri(n-butyl)methyl phosphonium bicarbonate salt to catalyze the preparation of the corresponding diglycidyl ether from epichlorohydrin and bisphenol A. The resulting epoxy resin product is 29.01 grams of a light yellow (Gardner 6), viscous liquid for a yield of 90 mole percent based on bisphenol A. The observed epoxy content and epoxy equivalent weight of the product are 19.98 percent and 215, respectively. The product also contains 1.23 percent of total chlorine and greater than 1000 ppm of phenolic hydroxy groups. The viscosity of the freshly-prepared resin is 50,135 centipoise at 25° C. and increases to 71,634 centipoise at 25° C. after storage for 2 weeks at 25° C. The BTMAC catalyst, unlike the catalysts utilized in the instant novel process, causes instability of the resin product.

In order to demonstrate the relative thermal instability of the BTMAC-prepared product, 3.12 grams of epoxy resin-grade bisphenol A is added to 6.88 grams of product to produce a mixture having an observed epoxy content of 13.74 percent. After heating the mixture to 160° C. for 3 hours, the observed epoxy content is reduced to 7.91 percent.

EXAMPLE 6

In a manner otherwise similar to Example 5, 38.3 grams of the precatalyzed epichlorohydrin mixture (0.4 mole of epichlorohydrin) is added to 15.0 grams (0.1 mole) of p-t-butylphenol at 20° C. The mixture is heated to 120° C. and held at this temperature for 2 hours. The product mixture is then devolatilized and dehydrochlorinated as is described in Example 5. The 19.6 grams of product remaining after distillation is identified by conventional methods of analysis as p-t-butylphenylglycidyl ether. This represents a 92 percent yield based on the corresponding phenol reactant.

EXAMPLE 7

In a manner otherwise identical to Example 6, o-t-butylphenol is employed instead of the para isomer and the 120° C. reaction temperature is maintained for 6 hours. 18.5 Grams of o-t-butylphenylglycidyl ether is recovered representing a 90 percent yield based on the phenol reactant.

EXAMPLE 8

In a manner similar to that described in Example 4, a stirred mixture of 14.0 grams (0.048 mole) of trisphenol, 50.6 grams of epichlorohydrin and 0.260 gram of tri(n-butyl)methyl phosphonium bicarbonate salt in 65.5 percent solution of methanol is maintained at 150° C. for 1 hour. The reaction mixture is then cooled to 100° C. and distilled at reduced pressure (25 mm of Hg) to remove volatile components.

To the undistilled residue is added 40 ml of benzene and 50 ml of a 12 percent NaOH solution in water. The resulting triphasic mixture is refluxed for 2.5 hours and then the organic layer is separated and washed with water. Finally, the benzene and other volatiles are removed by distillation at 160° C. under reduced pressure to yield the final resin. The epoxy equivalent weight of the resin is 168.

EXAMPLE 9

To a mixture of 0.4 mole epichlorohydrin and 0.1 mole p-t-butylphenol is added 0.004 mole of n-butyl triphenyl phosphonium bicarbonate at 25° C. This stirred mixture is heated to 120° C. and held at this temperature for 2 hours. The product mixture is then devolatilized and dehydrochlorinated as described in Example 5. The 20.1 grams of product remaining after distillation is identified by conventional methods of analysis as p-t-butylphenylglycidyl ether. This represents a 94.3 percent isolated yield based on the corresponding phenol reactant.

What is claimed is:

1. A method of producing a glycidyl ether of a phenol comprising the steps of:
   (a) introducing a catalytic amount of a tri-n-butyl)methyl phosphonium bicarbonate salt into a liquid phase mixture of a phenol with excess epichlorohydrin to thereby produce at reactive conditions a coupled reaction product comprising the corresponding propylenechlorohydrin ether of said phenol; and
   (b) contacting the coupled reaction product in a liquid organic solvent with sufficient aqueous base in the presence of a catalytic amount of the tri(n-butyl)methyl phosphonium bicarbonate or its in situ derivative salts to convert the propylenechlorohydrin groups to glycidyl ether groups.

2. The process defined by claim 1 wherein step (a) is conducted at a temperature of from about 40° to about 200° C.

3. The process defined by claim 1 wherein step (a) is conducted at a temperature of from about 75° to 160° C.

4. The process defined by claim 1 wherein in step (b) said organic solvent is methylene chloride or toluene.

5. The process defined by claim 4 further comprising washing said organic solution of the glycidyl ether of a phenol from step (b) with water so as to effect removal of substantially all ionic chloride contaminants.

6. The process defined by claim 1 further comprising distilling the reaction product of step (a) to remove residual epichlorohydrin and 1,3-dichloropropanol from the reaction product prior to step (b).

7. The process defined by claim 1 wherein about 1.5 to about 20 equivalents of epichlorohydrin per phenolic hydroxyl group are present in step (a).

8. The process defined by claim 1 wherein the phenol reactant is represented by

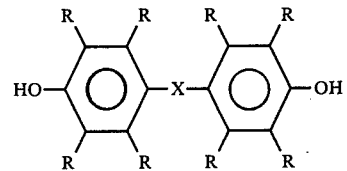

wherein each R independently is hydrogen, halogen or a hydrocarbyl radical and X is oxygen, sulfur, —SO—, —SO$_2$—, a bivalent hydrocarbon radical containing up to about 10 carbon atoms, —OR'O—, OR'OR'O—, —S—R'—S—, —S—R'—, —OSiO—, —OSiOSiO—,

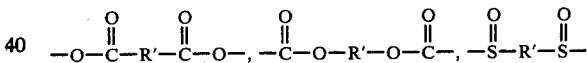

or —SO$_2$—R'—SO$_2$—radical, where R' is a bivalent hydrocarbon radical.

9. The process defined by claim 1 wherein
   (a) epichlorohydrin is reacted with bisphenol A in a ratio of about 1.5 to about 20 equivalent of a epichlorohydrin per phenolic hydroxyl group at a temperature of from about 140° C. to about 175° C. to produce a coupled reaction product; and
   (b) the coupled reaction product is contacted in a methylene chloride solution with sufficient sodium hydroxide in the presence of a catalytic amount of a tri(n-butyl)methyl phosphonium bicarbonate salt, so as to produce the diglycidyl ether of bisphenol A.

10. A process comprising introducing a catalytic amount of a tri(n-butyl)methyl phosphonium bicarbonate salt into a liquid phase medium containing a propylenechlorohydrin ether of a phenol in the presence of sufficient aqueous base, so as to convert the propylenechlorohydrin groups to glycidyl ether groups.

* * * * *

UNITED STATES PATENT AND TRADEMARK OFFICE
CERTIFICATE OF CORRECTION

PATENT NO. : 4,284,573
DATED : August 18, 1981
INVENTOR(S) : John F. Arnett and George A. Doorakian It is certified that error appears in the above—identified patent and that said Letters Patent is hereby corrected as shown below:

Column 6, line 67, "$HCO_3^{\oplus}$" should be -- $HCO_3^{\ominus}$ --;

Column 11, line 53, "tri-n-butyl)-" should be -- tri(n-butyl)- --;

Column 12, line 7, after "to" insert -- about --;

Column 12, line 36, after "-S-R'-," insert -- -S-R'-S-R'-S-, --;

Column 12, line 41, "where" should be -- wherein --;

Column 12, line 46, "equivalent" should be plural.

Signed and Sealed this

Twenty-seventh Day of April 1982

|SEAL|

Attest:

GERALD J. MOSSINGHOFF

Attesting Officer

Commissioner of Patents and Trademarks